United States Patent
Fleury

(10) Patent No.: US 11,226,275 B2
(45) Date of Patent: Jan. 18, 2022

(54) METHOD FOR MEASURING THE DIFFUSION COEFFICIENT OF WATER WITHIN A POROUS MEDIUM BY A NUCLEAR MAGNETIC RESONANCE METHOD

(71) Applicant: IFP Energies nouvelles, Rueil-Malmaison (FR)

(72) Inventor: Marc Fleury, La Celle Saint Cloud (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 91 days.

(21) Appl. No.: 16/621,587

(22) PCT Filed: May 15, 2018

(86) PCT No.: PCT/EP2018/062583
§ 371 (c)(1),
(2) Date: Dec. 11, 2019

(87) PCT Pub. No.: WO2018/233936
PCT Pub. Date: Dec. 27, 2018

(65) Prior Publication Data
US 2020/0116616 A1    Apr. 16, 2020

(30) Foreign Application Priority Data

Jun. 19, 2017    (FR) .................... 1755552

(51) Int. Cl.
*G01N 13/00*    (2006.01)
*G01N 24/08*    (2006.01)
*G01N 33/38*    (2006.01)

(52) U.S. Cl.
CPC .......... *G01N 13/00* (2013.01); *G01N 24/081* (2013.01); *G01N 33/383* (2013.01); *G01N 2013/003* (2013.01)

(58) Field of Classification Search
None
See application file for complete search history.

(56) References Cited

U.S. PATENT DOCUMENTS

| | | | |
|---|---|---|---|
| 2005/0168220 A1* | 8/2005 | Lenormand | G01R 33/44 324/303 |
| 2006/0132131 A1* | 6/2006 | Fleury | G01N 15/0826 324/307 |

OTHER PUBLICATIONS

Fleury et al. "Diffusion of dissolved CO2 in caprock" Energy Procedia, (Year: 2009).*
Weisenberger et al. "NMR imaging of solvent diffusion in polymers" Applied Spectroscopy (Year: 1989).*

* cited by examiner

*Primary Examiner* — Douglas X Rodriguez
(74) *Attorney, Agent, or Firm* — Fitch, Even, Tabin & Flannery LLP

(57) ABSTRACT

The present invention relates to a method of measuring the diffusion coefficient of water in a porous medium. The coefficient is measured using a nuclear magnetic resonance (NMR) technique (2, 3, 4) and the sample (1) has the shape of a hollow cylinder.

19 Claims, 3 Drawing Sheets

METHOD FOR MEASURING THE DIFFUSION COEFFICIENT OF WATER WITHIN A POROUS MEDIUM BY A NUCLEAR MAGNETIC RESONANCE METHOD

CROSS REFERENCE TO RELATED APPLICATIONS

Reference is made International Application No. PCT/EP2018/062583, filed May 15, 2018, which claims priority to French Application No. 17/55.552 filed Jun. 19, 2017, which applications are incorporated herein by reference in their entirety.

BACKGROUND OF THE INVENTION

Field of the Invention

The present invention relates to the field of measuring the diffusion coefficient of water in a porous medium and in particular cement paste, concrete or a compact rock from an underground formation.

Description of the Prior Art

Diffusion properties in porous media are a significant parameter in some applications. For example, when it is desired to store liquids or gases in geological layers, the cap rock present above the storage zone must act as a barrier against stored gas or liquid transportation. In the context of nuclear waste, the cementitious materials surrounding the waste must also act as a barrier and have the lowest possible diffusion properties.

In general, measuring diffusion properties in porous media takes a long time. A well-known method used for many years is the through-diffusion technique. Such a method is described notably in the document C. D. Shackelford, Journal of Contaminant Hydrology 7 (1991), 177-217. The porous material to be tested is cut into a disc. One of the faces (upstream) of the disc is contacted with the diffusing liquid (water for example) to which a tracer (tritiated water for example) has been added. The other face (downstream) is also contacted with the liquid, but in the absence of a tracer. Regular sampling downstream from the sample and measurement of the tracer concentration then allows determination of the diffusion coefficient of the liquid considered in the porous medium.

Methods using Nuclear Magnetic Resonance (NMR, pulsed gradients) are also known to allow measurement of the diffusion coefficients without however requiring a tracer. For example, to measure the self-diffusion coefficient of water, the position of the molecules can be spatially encoded in a similar manner to NMR imaging and diffusion coefficients can be deduced in very varied situations. The NMR technique is however possible only if the magnetization generated in the sample has a sufficiently long lifetime, which requires long enough relaxation times. Typically, the time required for magnetization encoding is of the order of 10 ms, and therefore the relaxation times need to have the same order of magnitude. This is not the case in cementitious media or compact geological media (cap rock) for which relaxation times are around 1 ms or less. These low relaxation times do therefore not allow diffusion coefficients to be measured using the conventional NMR technique.

To overcome this problem, a diffusion technique using a deuterium tracer has been developed. This technique is notably described in the document P. Berne, P. Bachaud, M. Fleury, Oil & Gas Science and Technology—Revue de l' Institut Français du Pétrole 65 (2009), 473-484. This NMR technique generally enables faster measurement than the through-diffusion technique. However, for cementitious materials, diffusion measurement in these materials takes a longer time because the diffusion coefficients are low (of the order of $10^{-12}$ m$^2$/s). For example, for a cement paste sample, the duration of an NMR measurement is of the order of 200 hours, which remains high for this type of material.

In general, the NMR technique becomes faster as the sample becomes smaller. This is also true for the conventional technique where the thickness of the sample is an important parameter. Now, for some materials, the dimensions of the sample cannot be reduced below certain values. For example, fora concrete containing aggregates a few millimeters in size (up to one centimeter), the dimensions of the samples must be kept large enough in relation to the size of these heterogeneities. Thus, for such materials, measuring the diffusion coefficient requires substantial time since a large-size sample is needed.

SUMMARY OF THE INVENTION

To overcome these drawbacks, the present invention is a method of measuring the diffusion coefficient of water in a porous medium, wherein the coefficient is measured using an NMR technique and the sample has the shape of a hollow cylinder. This specific shape of the sample allows measurement of the diffusion coefficient by an NMR technique more rapidly for any type of material, including concretes containing large-size aggregates.

The invention is a method of measuring the diffusion coefficient of water in a porous medium including the following steps:

a) preparing a sample of the porous medium in a hollow cylinder;

b) saturating the sample of the porous medium with water;

c) immersing the water-saturated sample of the porous medium in a water-miscible tracer fluid which is not detectable by a Nuclear Magnetic Resonance NMR method;

d) measuring the water concentration in the sample using a Nuclear Magnetic Resonance (NMR) method; and e) determining the water diffusion coefficient in the porous medium by use of the measured water concentration in the sample, by accounting for the hollow cylindrical shape of the sample of the porous medium.

According to an embodiment of the invention, the porous medium is a cement paste, concrete or rock.

Advantageously, the concrete contains aggregates that are a few millimeters in size.

According to an implementation, the outside diameter of the hollow cylinder ranges between 20 and 80 mm, and the inside diameter of the hollow cylinder ranges between 2 and 25 mm.

According to a characteristic, the tracer fluid which is not detected by a Nuclear Magnetic Resonance NMR method is deuterium.

According to an embodiment, the hollow cylinder is formed by double coring of the porous medium.

Advantageously, the diffusion coefficient $D_p$ of the water in the porous medium is determined by use of a formula:

$$C^* = C_{ps} C_{cylcreux}$$

-continued with $$C_{ps} = \sum_{n=0}^{\infty} \frac{8}{(2n+1)^2\pi^2} \exp\left(-D_p(2n+1)^2\pi^2 \frac{t}{4l^2}\right),$$

$$C_{cylcreux} = \frac{4}{b^2-a^2} \sum_{n=0}^{\infty} \frac{J_0(ak_n) - J_0(bk_n)}{k_n^2(J_0(ak_n) + J_0(bk_n))} \exp(-D_p k_n^2 t),$$

Wherein:
C* is the measurement of the water concentration within the sample;
2l is the length of the sample;
a is the inside diameter of the sample;
b is the outside diameter of the sample;
$J_0$ is the Bessel function of the first kind of order 0;
$Y_0$ is the Bessel function of the second kind of order 0;
$k_n$ is the positive solutions to equation $J_0(ak_n)Y_0(bk_n)-J_0(bk_n)Y_0(ak_n)=0$; and
t is time.

Furthermore, the invention relates to a method of storing a fluid in an underground formation, wherein the following steps are carried out:
a) determining the water diffusion coefficient within at least one rock overlying the underground formation by use of the diffusion coefficient measurement method according to one of the previous characteristics; and
b) storing the fluid in the underground formation if the diffusion coefficient is below a predetermined threshold that ensures non-dispersion of the fluid to be stored in the rock overlying the underground formation.

Preferably, the fluid to be stored is an acid gas, notably $CO_2$.

Moreover, the invention is a method of storing a radioactive material in an enclosure, wherein the following steps are carried out:
a) determining the water diffusion coefficient within cement pastes by use of the diffusion coefficient measurement method according to one of the previous characteristics;
b) constructing the enclosure with the cement paste having the lowest diffusion coefficient; and
c) storing the radioactive material within the cement enclosure.

BRIEF DESCRIPTION OF THE DRAWINGS

Other features and advantages of the method according to the invention will be clear from reading the description hereafter of non-limitative example embodiments, with reference to the accompanying figures wherein.

DETAILED DESCRIPTION OF THE INVENTION

Figure 1:
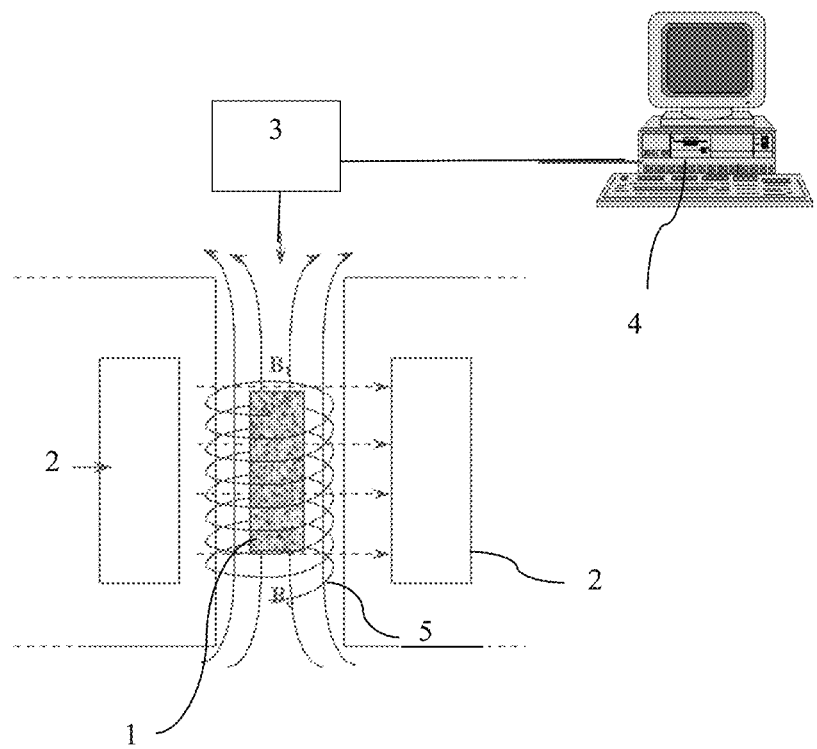
FIG. 1 illustrates NMR measurement apparatus.

The present invention relates to a method of measuring the diffusion coefficient of water in a porous medium. The diffusion coefficient of water in a porous medium is a characteristic of a porous medium that depends, in relation to the diffusion properties of water outside a porous medium, first on the porosity, then on the structure of the porous medium (tortuosity).

The porous medium concerned can be a cement paste, a concrete, a rock, or any similar medium. For example, the porous medium can be a concrete containing aggregates (crushed rocks for example) which are a few millimeters in size.

According to the invention, the method of measuring the diffusion coefficient of water in a porous medium comprises the following steps:
a) preparing a sample of the porous medium in a hollow cylinder, by double coring for example;
b) saturating the porous medium sample with water;
c) immersing the saturated porous sample in a water-miscible tracer fluid which is not dectable by a Nuclear Magnetic Resonance NMR method, deuterium for example;
d) measuring the water concentration in the porous medium sample using a Nuclear Magnetic Resonance NMR method; and
e) determining the water diffusion coefficient in the porous medium by use of the measured water concentration in the sample, by accounting for the hollow cylinder shape of the porous medium sample.

The hollow cylinder shape of the sample allows the measurement time to be reduced while keeping sufficient sample dimensions, notably for materials containing aggregates, to enable diffusion coefficient measurement by using an NMR technique. It is thus possible to reduce the measurement time of the diffusion coefficient of water in the porous medium, and for all materials.

Furthermore, the NMR method affords the advantage of being four to ten times faster than the standard method (through-diffusion method) for the same sample size.

According to an embodiment of the invention, the shape of the hollow cylinder is taken into account by use of a shape factor that notably depends on the inside and outside diameters of the sample. Thus, measurement of the diffusion coefficient is suited to the specific shape of the sample.

According to an embodiment option, the dimensions of the hollow cylinder verify the following conditions:
The outside diameter of the hollow cylinder ranges between 20 and 80 mm. These dimensions provide a sample of sufficient size, notably for concretes containing aggregates;
The inside diameter of the hollow cylinder ranges between 2 and 25 mm. These dimensions provide a measurement time gain while maintaining a sufficient sample volume for measurement.

Moreover, the length of the hollow cylinder can range between 10 and 100 mm.

According to an implementation of the invention, the inside diameter of the hollow cylinder can range between 2 and 50% of the outside diameter of the hollow cylinder, which provides a measurement time gain while maintaining a sufficient sample volume for measurement. Preferably, the inside diameter of the hollow cylinder can range between 15 and 30% of the outside diameter to optimize the measurement time gain while maintaining a sufficient sample volume for measurement.

According to an embodiment of the invention, an NMR apparatus can be used without any modification. In particular, NMR apparatuses made from permanent magnets having magnetic fields around 0.5 T are perfectly suitable. These are in fact produced at a lower cost. These apparatuses generally comprise permanent magnets, a solenoid acting as a transmitting and receiving antenna, and suitable electronics allowing generation of NMR pulse sequences. The radiofrequency field can be adjusted for detection of protons (and not deuterons) according to Larmor's law. The presence of specific coils allowing pulsed field gradients is not necessary. An apparatus geometry suited to the size of the analyzed sample can be selected to optimize the filling factor of the antenna and therefore the signal/noise ratio.

FIG. 1 schematically illustrates, by way of non-limitative example, an NMR apparatus that can be used for the method according to the invention. In this NMR apparatus, the water-saturated sample 1 is placed in a first magnetic field $B_0$ (substantially vertical curved arrows) made up of two magnets 2 and a second magnetic field $B_1$ (dotted rectilinear arrows) made up of a solenoid 5. The NMR measuring apparatus further comprises a control 3 that may include a generator of NMR pulse sequences, temperature regulation, an amplifier, magnet and solenoid control, and electronics. Furthermore, the NMR measuring apparatus can comprise computer 4 for automating and saving the measurements that are performed.

According to an implementation of the invention, the principle of NMR measurement using a deuterium tracer can be as follows. A sample of the porous medium initially saturated with water is placed in a tube, a glass tube for example, suited to the NMR apparatus used. This sample is then dipped in deuterium (which defines the time zero of the experiment). It is to be recalled that deuterium is heavy water in form of an isotope of water. The principle of this implementation of the invention is to have two miscible liquids, one of which is not detected by NMR, or more exactly not detected by NMR because the NMR measuring apparatus is set for the first fluid, water. It is to be noted that deuterium can be detected with an NMR method, but this detection requires an NMR apparatus setup for deuterium and not water. Diffusion of the two species then starts with the deuterium entering the sample and the water leaving the sample. An NMR relaxation measurement technique allows measurement of the amount of water within the sample, without being affected by the water outside the sample, which has a very long relaxation time. The deuterium is not detected at any time because the apparatus is set for detection of protons in water. The NMR measurement using a deuterium tracer as described here is akin to a so-called in-diffusion measurement, which uses the terminology employed for radionuclides. In practice, the tube may not be permanently placed in the NMR apparatus if the kinetics are slow. Indeed, the sealed glass tube can be stored in an oven at the same temperature as that of the NMR apparatus is substantially 30° C. for example.

The NMR measurement method applied for the method according to the invention can be the one described in the document: P. Berne, P. Bachaud, M. Fleury, Oil & Gas Science and Technology—Revue de l'Institut Français du Pétrole 65 (2009), 473-484, using a sample in a form of a hollow cylinder.

The data measured by the apparatus is the magnetization generated by the proton population within the sample as a function of time M(t). The analysed data is the relative water concentration C* within the sample as a function of time obtained by normalizing magnetization M(t) with M(t=0) and M(t=∞), without requiring calibration of the signal with only the signal proportionality hypothesis with the amount of protons being necessary.

The relative water concentration C* within the sample can be determined from the magnetization measurements using an equation:

$$C^* = \frac{M(t) - M(t=\infty)}{M(t=0) - M(t=\infty)}$$

In the case of a hollow cylindrical shape, the following analytical equations can be used to determine the diffusion coefficient:

$$C^* = C_{ps} C_{cylcreux}$$

with $$C_{ps} = \sum_{n=0}^{\infty} \frac{8}{(2n+1)^2 \pi^2} \exp\left(-D_p (2n+1)^2 \pi^2 \frac{t}{4l^2}\right),$$

$$C_{cylcreux} = \frac{4}{b^2 - a^2} \sum_{n=0}^{\infty} \frac{J_0(ak_n) - J_0(bk_n)}{k_n^2 (J_0(ak_n) + J_0(bk_n))} \exp(-D_p k_n^2 t),$$

C* is the measurement of the water concentration within the sample (that can be obtained from the magnetization measurements by use of the equation described above);

2l is the length of the sample;

a is the inside diameter of the sample;

b is the outside diameter of the sample;

$J_0$ is the Bessel function of the first kind of order 0;

$Y_0$ is the Bessel function of the second kind of order 0;

$k_n$ are the positive solutions of equation $J_0(ak_n)Y_0(bk_n) - J_0(bk_n)Y_0(ak_n) = 0$; and t is time.

Thus, by use of these equations, the diffusion coefficient of the water in the porous medium can be determined from the measurement of the water concentration C* in the sample. In these equations, $C_{cylcreux}$ takes the shape of the sample into account.

Furthermore, the present invention relates to a method of storing a fluid in an underground formation. For this method, the following steps can be carried out:

a) determining the water diffusion coefficient within a rock from a layer overlying the storage zone of the underground formation by use of the diffusion coefficient measurement method as described above; and b) storing the fluid in the storage zone of the underground formation if the water diffusion coefficient within the overlying layer is below a predetermined threshold that ensures non-dispersion (in other words, preventing leakage) of the fluid to be stored towards the overlying layer of the storage zone of the underground formation.

This method ensures that the cap rock present above the underground formation acts as a barrier preventing transportation of the gas or the liquids stored which prevents gas or liquid leakage during or after storage.

Advantageously, for step a), a sample of the rock of a layer overlying the underground formation can be taken and a hollow cylinder is formed with this rock sample.

Preferably, the fluid to be stored in the underground formation is a gas, notably an acid gas, $CO_2$ for example.

The present invention further relates to a method of storing a radioactive material (radioactive waste for example) in an enclosure made from cement paste. For this method, the following steps can be carried out:

a) determining the water diffusion coefficient within cement pastes by use of the diffusion coefficient measurement method as described above, b) constructing an enclosure with the cement paste having the lowest water diffusion coefficient; and c) storing the radioactive material within the cement enclosure.

This method ensures that the cementitious materials surrounding the radioactive materials act as a barrier and have the lowest possible diffusion coefficients, which provides radioactive storage of material that prevents radioactive leakage.

Advantageously, for step a), a sample shaped as a hollow cylinder can be formed with each cement paste to be tested.

According to an embodiment of the invention, the storage enclosure may be buried in an underground formation.

APPLICATION EXAMPLES

The features and advantages of the method according to the invention will be clear from reading the application examples hereafter.

Figure 2:
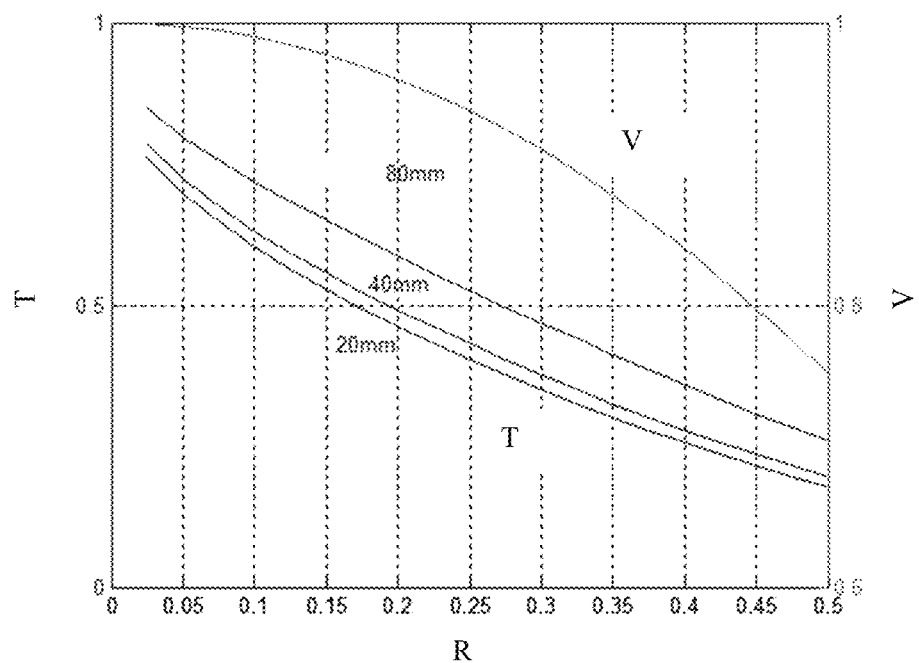
FIG. 2 is a comparative curve of the measurement times and volumes for a solid cylinder and for three hollow cylinders as a function of the ratio of the inside diameter to the outside diameter of the hollow cylinder.

In order to understand the advantage of performing a diffusion measurement in a sample in a hollow cylinder, three hollow cylinders used for the method according to the invention are compared with a solid cylinder used in the prior art for a fixed outside diameter of a sample. The samples used for the example have respective outside diameters of 20 mm, 40 mm and 80 mm. FIG. 2 illustrates this comparison for the measurement time T and the investigated volume V by taking the reference time and the measurement time and the investigated volume for the solid cylinder. It is found that measurement time T (indicated in a standardized manner in relation to the measurement time for a sample in form of a solid cylinder) decreases rapidly as a function of the inside diameter a of the hollow cylinder, whereas investigated volume V (indicated in a standardized manner in relation to the investigated volume for a sample in form of a solid cylinder) decreases little as a function of ratio R of the inside diameter to the outside diameter of the hollow cylinder. For example, the measurement time decreases by a factor of two for an inside diameter ranging between 15% and 28% of the outside diameter, whereas the investigated volume has decreased by only 5%. For a 40 mm concrete sample, the measurement time for a solid cylinder is of the order of one year. With the hollow cylinder geometry with an inside diameter ranging between 15% and 28% of the outside diameter according to the invention, the measurement time is thus reduced to 6 months or less.

This example shows that the method according to the invention allows reduction of the time required for measuring the diffusion coefficient of water in a porous medium, while maintaining dimensions suited to measurements for all types of materials.

Figure 3:
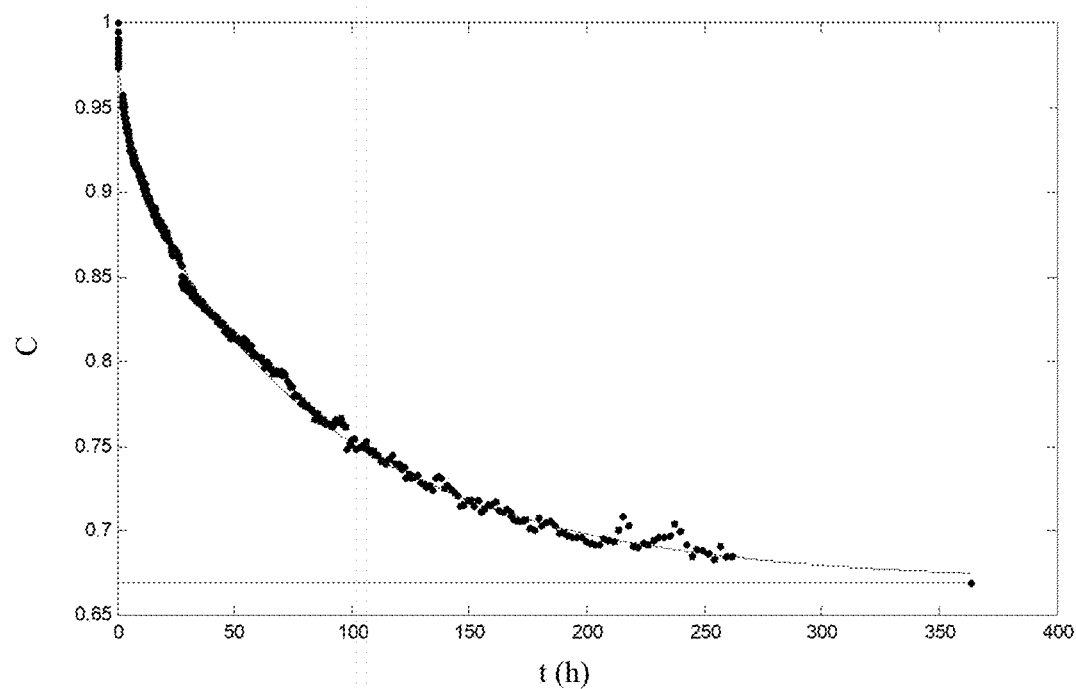
FIG. 3 is a curve of the diffusion coefficient measurement for a cement paste using the method according to the invention.

The second example relates to the measurement of a diffusion coefficient of water in a cement paste. For example, for such a material, the measurement times are approximately 350 hours with a hollow cylinder geometry having a hollow cylinder inside diameter a=11.0 mm, and a hollow cylinder outside diameter b=25.1 mm. FIG. 3 illustrates the relative water concentration C in the sample having the shape of a hollow cylinder (normalized) as a function of time t for this sample. The black points indicate the measurements. It is found that the method according to the invention allows the diffusion coefficient to be extracted. For this example, the diffusion coefficient of water in the cement paste is $D=1.3 \cdot 10^{-11}$ m$^2$/s. Measurement of the diffusion coefficient on a solid cylinder of same outside diameter requires more than 700 hours.

This example also shows that the method according to the invention allows reduction of the time required for measuring the diffusion coefficient of water in a porous medium.

The third example relates to the measurement of the diffusion coefficient of water in a Tavel calcareous rock. For this example, a hollow cylinder according to the invention was prepared by coring (outside diameter 25.18 mm, inside diameter 13.14 mm and length 26.73 mm) on the one hand, and on the other hand an inner cylinder (not hollow according to the prior art) from the same core was used as a reference (diameter 10.83 mm and length 18.60 mm). The volume of the first hollow cylinder is 5.7 times as great as the volume of the second solid sample. Two different apparatuses which at frequencies were used with one being at a frequency of 23 MHz (for the 11 mm-diameter sample of the prior art) and the other being at a frequency of 20 MHz (for the sample in form of a hollow cylinder according to the invention of outside diameter 25 mm).

The experimental characteristics are summarized in Table 1:

TABLE 1

Experimental characteristics of the third example

| | 1$^{st}$ sample Hollow cylinder | 2$^{nd}$ sample Cylinder |
|---|---|---|
| Diameters(s) (mm) | 25.18 13.14 | 10.83 |
| Length (mm) | 26.73 | 18.60 |
| Total volume (ml) | 9.68 | 1.71 |
| Pore volume (ml), porosity (%) | 1.29 13.3 | 0.20 11.8 |

Figure 4:
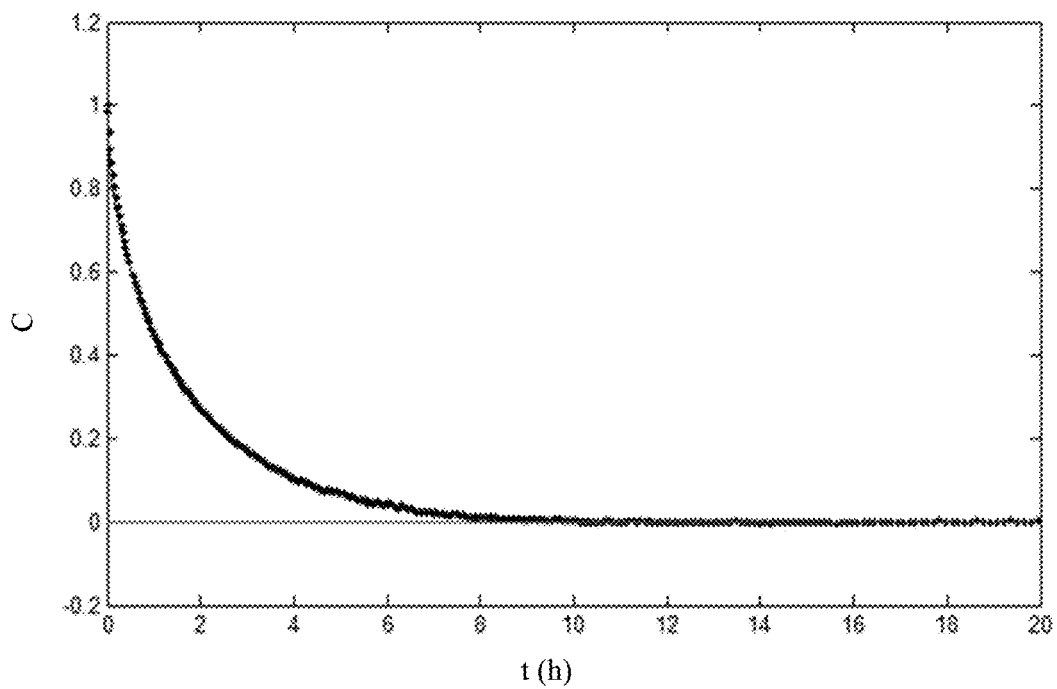
FIG. 4 is a curve of the diffusion coefficient measurement for a calcareous rock using the method according to the invention.

FIG. 4 illustrates the relative water concentration C in the first sample shaped as a hollow cylinder (normalized) as a function of time t. The black points indicate the measurements. It is found that the method according to the invention allows the diffusion coefficient to be extracted.

Figure 5:
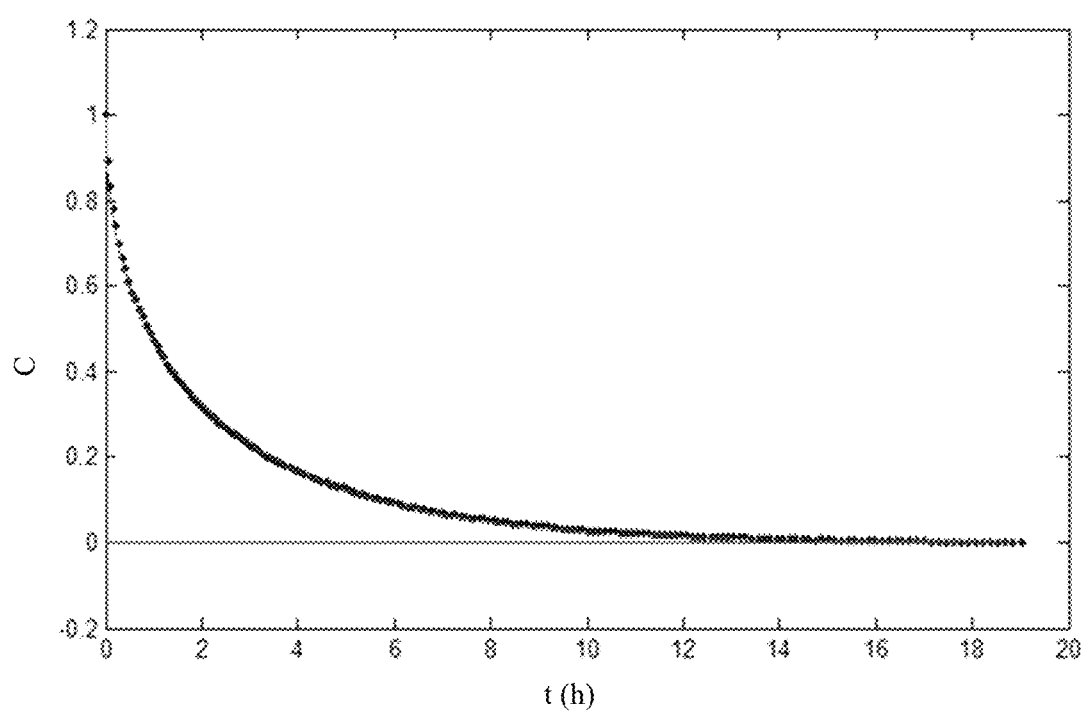
FIG. 5 is a curve of the diffusion coefficient measurement for a calcareous rock using a method according to the prior art.

FIG. 5 illustrates the relative water concentration C in the second sample shaped as a solid cylinder (normalized) as a function of time t. The black points indicate the measurements.

It can be noted that the water concentration (normalized between 1 and 0) measured in the two porous samples can be adjusted with the models with a very low error rate, of the order of 1%, except for very short times where the error reaches 4%. For the hollow cylinder according to the invention, the stabilization time is approximately 10 h, compared with 16 h for the solid cylinder. It can be inferred that the experiment that for the hollow cylinder is faster although the total volume of the sample is 5.7 times as large.

These three examples illustrate the measurement speed provided by the hollow cylinder shape of the sample for any type of porous material: concrete, cement paste, calcareous rock.

The invention claimed is:

1. A method of measuring a diffusion coefficient of water in a porous medium, comprising:

a) preparing a sample of the porous medium which is shaped as a hollow cylinder that only contains liquid during measurement of the diffusion coefficient with an inside diameter of the hollow cylinder ranging between 15 and 30% of an outside diameter of the hollow cylinder;

b) saturating the sample of the porous medium with water;
c) immersing the water-saturated sample of the porous medium in a water-miscible tracer fluid which is not detectable by a Nuclear Magnetic Resonance (NMR) method;
d) measuring the water concentration in the sample using an NMR method; and
e) determining the water diffusion coefficient in the porous medium by use of the measured water concentration in the sample which accounts for the shape of the hollow cylinder during measurement of the sample of the porous medium.

2. A method as claimed in claim 1, wherein the porous medium is one of a cement paste, concrete or rock.

3. A method as claimed in claim 2, wherein the concrete contains aggregates sized in millimeters.

4. A method as claimed in claim 3, wherein an outside diameter of the hollow cylinder ranges between 20 and 80 mm, and an inside diameter of the hollow cylinder ranges between 2 and 25 mm.

5. A method as claimed in claim 2, wherein an outside diameter of the hollow cylinder ranges between 20 and 80 mm, and an inside diameter of the hollow cylinder ranges between 2 and 25 mm.

6. A method as claimed in claim 2, wherein the tracer fluid which is not detectable by the NMR method is deuterium.

7. A method as claimed in claim 2, comprising:
double coring the porous medium.

8. A method as claimed in claim 1, wherein an outside diameter of the hollow cylinder ranges between 20 and 80 mm, and an inside diameter of the hollow cylinder ranges between 2 and 25 mm.

9. A method as claimed in claim 8, wherein the tracer fluid which is not detectable by the NMR method is deuterium.

10. A method as claimed in claim 8, comprising:
double coring the porous medium.

11. A method of storing a radioactive material in an enclosure, comprising:
a) determining a water diffusion coefficient within cement pastes by use of the diffusion coefficient measurement method as claimed in claim 8;
b) constructing the enclosure with a cement paste having a lowest diffusion coefficient of an available cement paste; and
c) storing the radioactive material within the cement enclosure.

12. A method as claimed in claim 1, wherein the tracer fluid which is not detectable by the NMR method is deuterium.

13. A method as claimed in claim 12, comprising:
double coring the porous medium.

14. A method as claimed in claim 1, comprising:
double coring the porous medium.

15. A method of storing a radioactive material in an enclosure, comprising:

a) determining a water diffusion coefficient within available cement pastes by use of the diffusion coefficient measurement method as claimed in claim 14;
b) constructing the enclosure with a cement paste having a lowest diffusion coefficient of cement paste; and
c) storing the radioactive material within the cement enclosure.

16. A method as claimed in claim 1, wherein the diffusion coefficient $D_p$ of the water in the porous medium is determined by a formula:

$$C^* = C_{ps} C_{cylcreux}$$

$$C_{ps} = \sum_{n=0}^{\infty} \frac{8}{(2n+1)^2 \pi^2} \exp\left(-D_p(2n+1)^2 \pi^2 \frac{t}{4l^2}\right),$$

$$C_{cylcreux} = \frac{4}{b^2 - a^2} \sum_{n=0}^{\infty} \frac{J_0(ak_n) - J_0(bk_n)}{k_n^2(J_0(ak_n) + J_0(bk_n))} \exp(-D_p k_n^2 t),$$

$C^*$ is the measurement of the water concentration within the sample;
$2l$ is the length of the sample;
a is the inside diameter of the sample;
b is the outside diameter of the sample;
$I_0$ is the Bessel function of the first kind of order 0;
$Y_0$ is the Bessel function of the second kind of order 0;
$k_n$ is the positive solutions to equation $J_0(ak_n)Y_0(bk_n)-J_0(bk_n)Y_0(ak_n)=0$; and
t is time.

17. A method of storing a fluid in an underground formation, comprising:
a) determining a water diffusion coefficient within at least one rock overlying the underground formation by use of the diffusion coefficient measurement method as claimed in claim 1; and
b) storing the fluid in the underground formation if the diffusion coefficient is below a predetermined threshold that ensures non-dispersion of the fluid to be stored in the rock overlying the underground formation.

18. A method as claimed in claim 17, wherein the fluid to be stored is an acid gas.

19. A method of storing a radioactive material in a cement enclosure, comprising:
a) determining a water diffusion coefficient within cement pastes by use of the diffusion coefficient measurement method as claimed in claim 1;
b) constructing the cement enclosure with a cement paste having a lowest diffusion coefficient of available cement paste; and
c) storing the radioactive material within the cement enclosure.

* * * * *